United States Patent
Lukas

(10) Patent No.: US 10,105,458 B2
(45) Date of Patent: Oct. 23, 2018

(54) DRY HEAT SANITIZER AND METHOD OF USE

(71) Applicant: K&K Lukas LLC, Hillsboro, OR (US)

(72) Inventor: Kevin Lukas, Hillsboro, OR (US)

(73) Assignee: K&K Lukas LLC, Hillsboro, OR (US)

( * ) Notice: Subject to any disclaimer, the term of this patent is extended or adjusted under 35 U.S.C. 154(b) by 0 days.

(21) Appl. No.: 15/055,320

(22) Filed: Feb. 26, 2016

(65) Prior Publication Data
US 2016/0250361 A1    Sep. 1, 2016

Related U.S. Application Data

(60) Provisional application No. 62/121,011, filed on Feb. 26, 2015.

(51) Int. Cl.
*A61L 2/04*    (2006.01)
*A61B 90/70*    (2016.01)
*A61C 19/00*    (2006.01)

(52) U.S. Cl.
CPC .............. *A61L 2/04* (2013.01); *A61B 90/70* (2016.02); *A61C 19/002* (2013.01)

(58) Field of Classification Search
CPC .......... A61L 2/04; A61B 90/70; A61C 19/002
See application file for complete search history.

(56) References Cited

U.S. PATENT DOCUMENTS

| | | |
|---|---|---|
| 4,050,894 A | 9/1977 | Genis |
| 4,376,096 A | 3/1983 | Bowen |
| 4,617,178 A | 10/1986 | Nichols |
| 4,663,122 A | 5/1987 | Sparks |
| 4,728,504 A | 3/1988 | Nichols |
| 4,923,681 A | 5/1990 | Cox et al. |

(Continued)

FOREIGN PATENT DOCUMENTS

| | | | |
|---|---|---|---|
| CA | 2268042 A1 * | 10/2000 | ............... A61L 2/07 |
| EP | 2510953 A1 | 10/2012 | |

(Continued)

OTHER PUBLICATIONS

International search report and written opinion dated Jun. 2, 2016 for PCT/US2016/019936.

*Primary Examiner* — Regina M Yoo
(74) *Attorney, Agent, or Firm* — Sheridan Ross P.C.

(57) ABSTRACT

A sanitizer system and method of use is disclosed. The sanitizer system quickly sanitizes and cools targeted objects and secures the targeted sanitized objects for later use, without the need to transfer the objects to a separate container. In one embodiment, the sanitizer system comprises a cassette having a body and a removable lid that, when joined, form an airtight chamber for containing an object for sterilization. A pressure control element of the system is configured to fluidly engage with the cassette to produce a pressure-controlled environment within the airtight chamber. A heating element of the system, which is interconnected and in thermal communication with the airtight chamber, is configured to provide heat to the airtight chamber. The chamber temperature is raised to a desired temperature for a period of time sufficient to sanitize the object. A cooling element of the system is configured to cool the chamber and the object.

13 Claims, 12 Drawing Sheets

(56) References Cited

U.S. PATENT DOCUMENTS

| | | | |
|---|---|---|---|
| 5,140,136 A * | 8/1992 | Fellows | A61L 2/26 219/386 |
| 5,290,511 A * | 3/1994 | Newman | A61L 2/07 422/26 |
| 5,353,930 A | 10/1994 | Berry, Jr. | |
| 5,396,049 A | 3/1995 | Knopf | |
| 5,443,801 A | 8/1995 | Langford | |
| 5,520,892 A * | 5/1996 | Bowen | A61C 19/002 422/295 |
| 5,543,119 A | 8/1996 | Sutter et al. | |
| 6,039,926 A | 3/2000 | Goldman | |
| 7,018,592 B2 * | 3/2006 | Bowen | A61L 2/07 422/26 |
| 7,641,852 B1 | 1/2010 | McPhail et al. | |
| 7,708,960 B2 | 5/2010 | Snyder et al. | |
| 7,803,317 B2 * | 9/2010 | Toepfer | A61L 2/04 422/28 |
| 8,327,606 B2 * | 12/2012 | Kemp | A61L 2/07 422/26 |
| 8,815,174 B2 | 8/2014 | Bacik et al. | |
| 2003/0211023 A1 | 11/2003 | Wu et al. | |
| 2004/0001783 A1 * | 1/2004 | Bowen | A61L 2/07 422/292 |
| 2010/0186780 A1 * | 7/2010 | Larocca | A61C 19/002 134/105 |
| 2011/0262301 A1 | 10/2011 | Ghelman et al. | |
| 2012/0152289 A1 * | 6/2012 | Smith | A61L 2/26 134/109 |
| 2012/0251384 A1 | 10/2012 | Sedlacek et al. | |
| 2013/0078161 A1 | 3/2013 | Smith et al. | |
| 2015/0139858 A1 * | 5/2015 | Pedrazzi | A61L 2/07 422/109 |

FOREIGN PATENT DOCUMENTS

| | | | |
|---|---|---|---|
| WO | WO-9312841 A1 | 7/1993 | |
| WO | WO-0059552 A1 * | 10/2000 | A61L 2/07 |
| WO | WO-2014104940 A1 | 7/2014 | |
| WO | WO-2014159696 A1 | 10/2014 | |

* cited by examiner

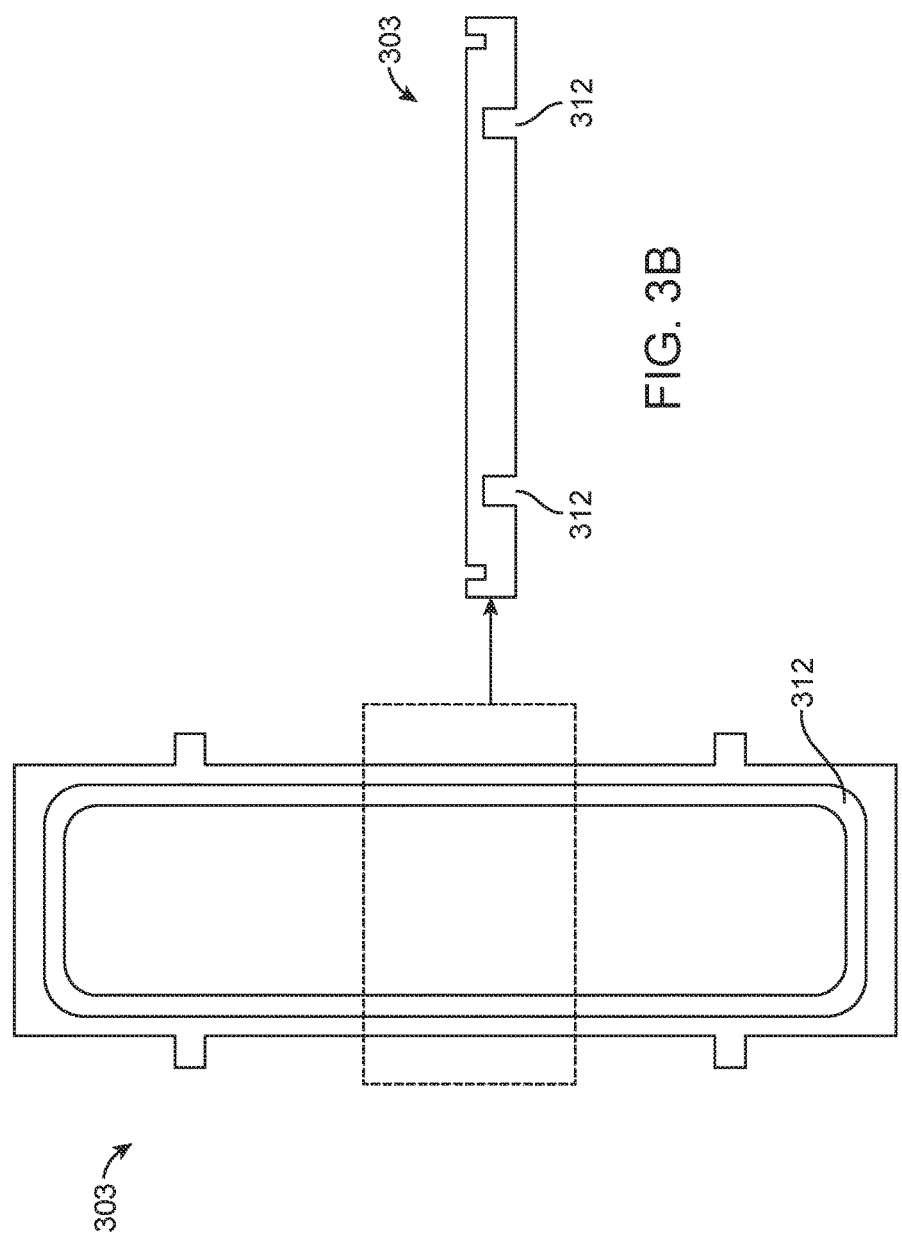

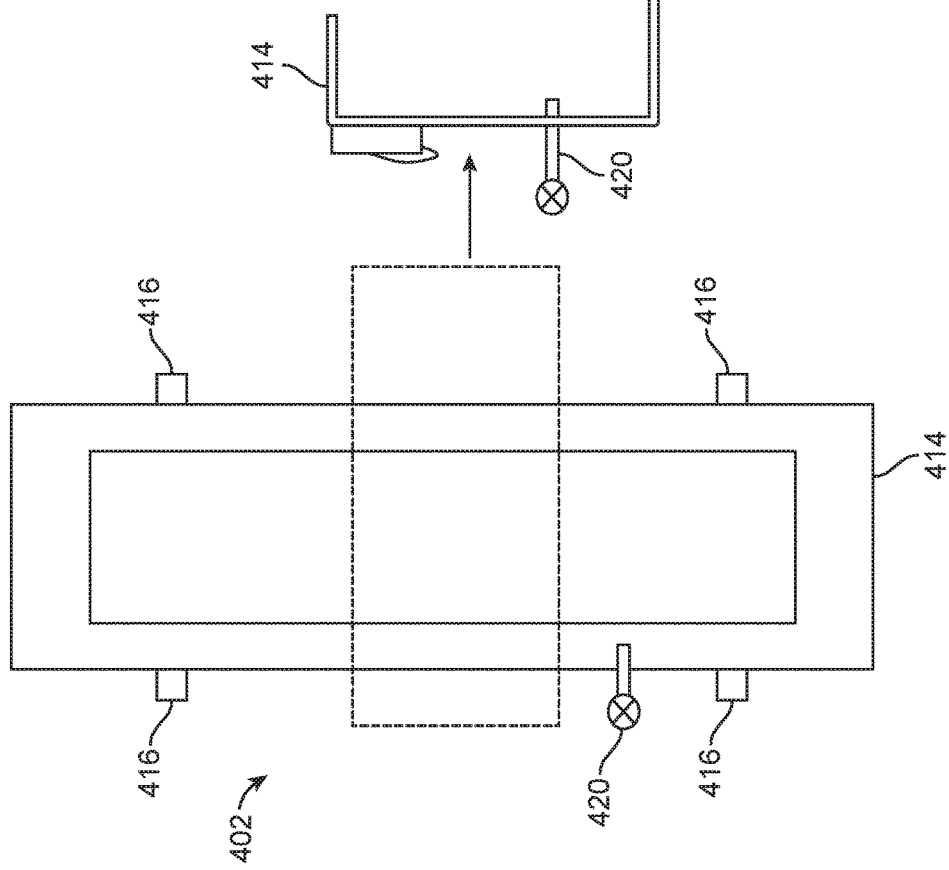

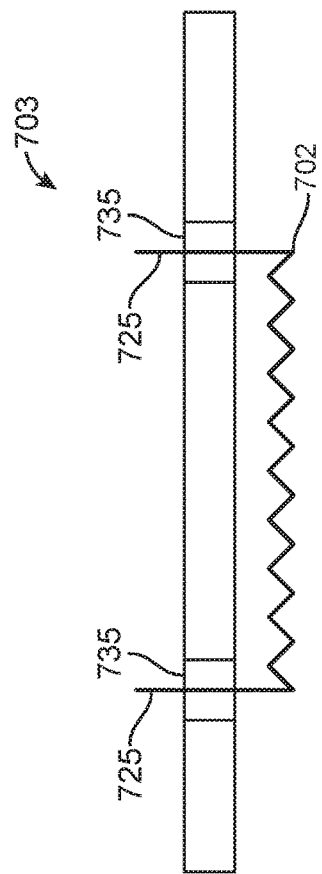
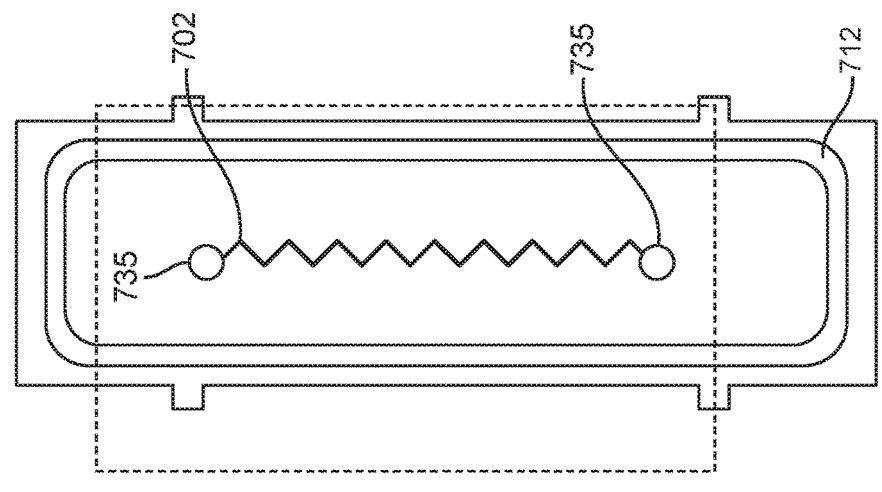
FIG. 7B
FIG. 7A

DRY HEAT SANITIZER AND METHOD OF USE

CROSS-REFERENCE

This application claims the benefit of U.S. Provisional Application No. 62/121,011, filed Feb. 26, 2015, which application is incorporated herein by reference.

BACKGROUND OF THE INVENTION

Field of the Invention

Embodiments are generally related to a sanitizing system, and, in particular, to a dry heat sanitizer and method of use.

Existing sanitizing systems use a variety of sanitizing means to clean, reduce microbial contamination, or sterilize equipment. Each of the sanitizing means carry relative limitations such as time required to clean or sterilize the targeted equipment, total cycle time to include any heating or cooling-off time, stress or wear to the targeted equipment, material composition requirements, sanitizing temperature, energy or power demands, and management of the targeted equipment once cleaned or sterilized. The existing systems provide a compromise of the above limitations. Conventionally, sanitized equipment is transferred to a separate container or sealed bag prior to use, e.g. in a dental care application.

Existing dry heat methods of sanitization have relatively slower cool-to-cool cycle time, i.e. the total cycle time from start to finish of the sanitization process or from insertion to removal of the cool instruments, including any heating or cooling-off time. Furthermore, with new standards for infection control, dry heat poses an elongated sanitization time, especially when needing to bag the sanitized instruments. A longer sanitization time requires an office to keep more instruments on hand to keep up with the number of patients being attended. Present standards require bagging within a reasonable time after sanitization, meaning the instruments come into contact with the ambient environment after sanitization, which can contaminate the sanitized instruments.

Autoclaves utilizing steam have relatively decreased cycle time (due to the lower temperature requirements) and can be bagged pre-sanitization. However, the steam is known to dull instruments, leading to higher cost in instrument purchase from decreased instrument lifetime. Another issue with bagging is there is no way to determine if the sanitized bag has been contaminated post sanitization, by the ambient environment or other factors, due to a hole or perforation in the bag (typically not visible to the naked eye). Finally, the use of bags in general and necessity for water in steam autoclaves are not eco-friendly because the plastic is disposed of after each use and the water must be continually replenished.

Existing dry heat sanitizers work by convection: air in a chamber is heated and flows around stainless steel instruments. Some issued US patents describe different patterns of air flow and designs of cassettes (containers) that hold the instruments. Some designs load instruments in a rack or shelf in the sanitizer. Typical dry heat sanitization time/temperature is 6 minutes at 375° F. Usually the instruments are left in the chamber to cool; one important variable is total cycle time from insertion to removal of the cool instruments—typically a 40 minute cycle.

Current practice in a dental or medical office is to remove sanitized instruments when cool and place them in bags until needed for a patient. Disadvantages of this approach include cost of the bags. Furthermore, several states have laws and/or regulations that require instruments to be bagged after removal from a dry heat sanitizer or sterilizer.

A conventional approach to sanitization of medical equipment is through convection, such as by blowing hot air over objects targeted for sanitization. U.S. Pat. Nos. 4,923,681 and 6,039,926, and U.S. Patent Application Publication No. 2013/0078161, each of which is incorporated herein by reference in its entirety, provide examples of this conventional approach. Generally, the convection-style sterilizing devices, as disclosed in the examples listed above, have practical operational deficiencies. For example, once sanitized objects or instruments are removed from the sanitization device, they are exposed to ambient office conditions and will no longer be sterile. In some applications (e.g. typical hospital applications), if sanitized instruments are not used immediately, the instruments must be maintained as sanitized until used. Thus, it would be advantageous to provide a single container that overcomes some of these challenges. In dental applications, instruments can be bagged prior to sanitization and will remain sanitized in the bag until opened. However, the cost and waste associated with the use of bags that may be sanitized or sterilized is preferred to be avoided, thus again motivating a single container that avoids or overcomes some of these issues.

Other conventional approaches to sanitization using heat include U.S. Pat. Nos. 4,376,096 and 5,396,049, WO 93/12841, and WO 2014/104940, each of which is incorporated herein by reference in its entirety. Additionally, efforts to improve the design of sanitization containers include, for example, U.S. Pat. Nos. 4,617,178, 5,353,930, WO 2014/159696 A1, U.S. Patent Application Publication No. 2003/0211023, and EP 2510953, each of which is incorporated herein by reference in its entirety.

It would therefore be advantageous to provide a sanitizing system and method of use that quickly sanitizes and cools targeted objects and secures the targeted sanitized objects for later use, without the need for transfer the sanitized objects to a separate container. This disclosure meets at least some of these objectives.

SUMMARY OF THE INVENTION

In one aspect, a sanitizer system comprises: a cassette comprising a body and a removable lid, the body and the removable lid forming an airtight chamber through an airtight seal when joined together, the airtight chamber configured to contain an object for sanitization; a pressure control element configured to fluidly engage with the cassette and produce a pressure-controlled environment within the airtight chamber; a heating element in thermal communication with the airtight chamber, the heating element configured to provide heat to the airtight chamber; wherein the heat provided by the heating element raises a temperature within the airtight chamber to a desired temperature and for a period of time sufficient to sanitize the object for sanitization; and a cooling element in thermal communication with the airtight chamber, the cooling element configured to lower the temperature within the airtight chamber such that the object for sanitization is cooled.

The thermal communication between the heating element and the airtight chamber and the thermal communication between the cooling element and the airtight chamber of the sanitizer system may be via thermal conduction or thermal convection. In addition, the heating element may be in surface contact with the cassette and may also further comprise a plurality of elongated heating members separated by alternating gaps forming a heating platform having a substantially planar heating surface, wherein the heating platform conducts heat in a substantially even manner over a surface of the cassette. Alternatively, the heating element may be disposed inside the cassette to heat the airtight chamber and may further comprise electrical contacts exiting the lid of the cassette through sealed openings.

The cooling element of the sanitizer system may comprise an active cooling element, including for example, a thermoelectric cooler. The cooling element may be configured to be in surface contact with the cassette such that the cooling element reduces the temperature of the cassette. In addition, the cooling element may further comprise a plurality of elongated cooling members separated by alternating gaps forming a cooling platform having a substantially planar cooling surface.

The sanitizer system may further comprise an actuator element, wherein the actuator element is configured to move one of the heating or cooling element relative to the other of the heating or cooling element. Moreover, the cassette may only be in surface contact with one of the heating or cooling element when it is in a raised or a lowered position with respect to the other of the heating or the cooling element. One of the heating or cooling element may comprise an opening therein and the other of the heating or cooling element may be moved through the opening into a raised or lowered position relative to the heating or cooling element with the opening.

The pressure control element may comprise a vacuum element configured to engage with the cassette and evacuate air from the airtight chamber to produce a vacuum environment therein, wherein the vacuum element may comprise a valve to control or monitor the vacuum environment, wherein the valve may be configured to provide an audible or visual indication that the airtight seal has been broken by actuating the valve from a closed position to an open position.

The sanitizer system may further comprise an indicator, such as, for example, a pressure gauge, having indicia that indicate a degree of pressure or vacuum established in the airtight chamber. The pressure control element of the sanitizer system may comprise an insertion element that may be configured to fluidly engage with the cassette and insert a fluid into the airtight chamber to produce a pressurized environment within the airtight chamber. The insertion element may comprise a valve to control or monitor the pressurized environment.

The sanitizer system may further comprise a filter, which may sanitize the fluid. The cassette may comprise an input and an output valve, wherein the input and the output valve may each have an open and a closed position, and wherein when both the input and the output valve are in the open position, filtered fluid may be delivered through the input valve filling the cassette with filtered fluid and forcing unfiltered fluid out of the output valve. The fluid may comprise a liquid or a gas, including but not limited to air, an inert gas, such as argon or neon, or a non-oxidizing gas, such as nitrogen.

The cassette may be removably disposed on the heating element or the cooling element of the sanitizer system. In addition, the cassette may comprise an alignment element on a top surface of the cassette and a mating element on a bottom surface of the cassette configured to align and mate with an adjacent cassette having an alignment element and a mating element.

The heat provided by the heating element may raise the temperature within the airtight chamber of the sanitizer system to a temperature and for a period of time sufficient to sterilize the object for sanitization to a level suitable for dental use or surgical use.

In another aspect, a method of sanitizing an object comprises: providing an object for sanitization; placing the object for sanitization within a cassette comprising a body and a removable lid; joining the body and removable lid of the cassette to form an airtight chamber containing the object for sanitization; controlling a pressure in the airtight chamber; heating the airtight chamber using a heating element to raise the temperature within the airtight chamber and thereby sanitizing the object for sanitization contained within the airtight chamber; maintaining the temperature for a designated period of time sufficient to sanitize the object for sanitization; and cooling the object for sanitization.

The method may further comprise moving one of the heating element or a cooling element relative to the other of the heating element or cooling element such that the cassette is only in surface contact with either the heating element or the cooling element. One of the heating element or the cooling element may comprise an opening, and the method may further comprise moving or passing one of the heating element or the cooling element through the opening in the other of the heating element or the cooling element. Heating the airtight chamber may comprise heating the airtight chamber through thermal conduction, through thermal convection, by contacting a surface of the cassette with the heating element, or by heating with the heater element disposed inside the cassette. Cooling the object for sanitization may comprise contacting a surface of the cassette with a cooling element and may further comprise active cooling, including for example, thermoelectrically cooling. Placing the object for sanitization within the cassette may comprise placing the object such that it is in surface contact with the cassette.

Producing a pressure-controlled environment within the airtight chamber containing the object for sanitization may comprise evacuating fluid from or disposing fluid into the airtight chamber to either decrease or increase the pressure in order to produce a vacuum or pressurized environment within the airtight chamber. The method may further comprise controlling or monitoring the vacuum or pressurized environment within the airtight chamber after the object for sanitization has been sanitized by using an audible, visual, or other indicator known in the art that the cassette is still under vacuum or is still pressurized. The cassette may comprise an input valve and an output valve, and the method may further comprise: opening the input valve, opening the output valve, passing a filtered fluid through the input valve into the chamber, forcing unfiltered fluid from the chamber through the output valve, pressurizing the chamber, and closing both valves. The method may further comprise removing the cassette from the heating element or the cooling element and may also comprise stacking the cassette on top of an adjacent cassette. Sanitizing the object for sanitation may further comprise sterilizing the object for sanitization to a level suitable for dental use or surgical use.

The terms "sanitize" and "sanitary" or variations thereof refer to actions needed, such as disinfecting or cleaning, to remove or reduce pathogenic microorganisms and their habitats from an object or an environment.

The term "sterilize" or variations thereof refers to sanitizing to a level suitable for dental use or surgical use, typically by bringing to a high temperature.

The term "autoclave" or variations thereof refers to an apparatus for sanitizing or sterilizing objects, such as surgical instruments, by means of steam under pressure.

The term "convection" or variations thereof refers to heat transfer through a gas or liquid by the circulation of currents from one region to another.

The term "conduction" or variations thereof refers to heat transfer through a conducting medium without perceptible motion of the medium itself, such as by a metallic connector medium.

The term "radiation" or variations thereof refers to the emission or transfer of radiant energy as particles, electromagnetic waves, sound, etc.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The accompanying drawings, which are incorporated in and constitute a part of the specification, illustrate embodiments of the invention and together with the general description of the invention given above, and the detailed description of the drawings given below, serve to explain the principals of this invention.

FIGS. 3A-3B show a top and cross-sectional side view respectively of a removable lid for a cassette;

FIGS. 4A-4B show a top and cross-sectional side view respectively of a cassette body;

FIGS. 7A-7B show a top and cross-sectional front view respectively of a removable cassette lid having an attached heating element;

It should be understood that the drawings are not necessarily to scale unless specifically so indicated. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION OF THE INVENTION

Generally, a sanitizer system and method of use that sanitizes, cools, and stores medical equipment using conduction and a removable cassette is disclosed. The system and method for sanitizing and storing instruments minimizes the potential for contamination during and post-sanitization while also providing a reduced cool-to-cool sanitization total cycle time. In one embodiment, the disclosed system reduces total cycle time from, for example, from between 50-60 minutes to between 15-20 minutes, preferably from between 35-40 minutes to between 12-15 minutes, and more preferably from between 30-35 minutes to between 9-10 minutes, allowing an office to manage its patient flow with fewer instruments resulting in a reduction in instrument cost.

The disclosed system may comprise a cassette having a removable lid and a cassette body joined to form an enclosed airtight chamber configured to hold objects or instruments for sanitization. The pressure within the cassette may be varied from the ambient environment by pulling air out of the chamber through a valve, or by disposing air, an inert gas, or some other fluid into the chamber to form a pressurized environment, essentially creating a mini vacuum or pressurized chamber. Once the objects or instruments have been placed in the cassette and a vacuum or pressurized chamber has been created, the cassette may be heated in the sanitizer system to an appropriate temperature for a time sufficient to sanitize the objects or instruments to a level suitable for the desired use. After sanitization of the objects or instruments, the cassette may be actively cooled, preferably to a temperature cool enough for a user to handle comfortably, and more preferably to room temperature, for either immediate use or for storage. To open and remove the objects or instruments post sanitization, a valve on the cassette may be turned from closed to open. After opening the valve, air may rush into the chamber through the valve producing an audible sound signifying that the chamber has been kept isolated from the ambient environment and is therefore uncontaminated post sterilization. Once the pressure inside the cassette has reached equilibrium with the ambient environment, the lid may be removed from the cassette body and the instruments, still disposed in the cassette, may be accessed for use. The disclosed device and method may be used in a variety of fields to include sanitization of medical, dental, pharmaceutical, cosmetic, surgical, and orthodontic objects or instruments.

Figure 1A:
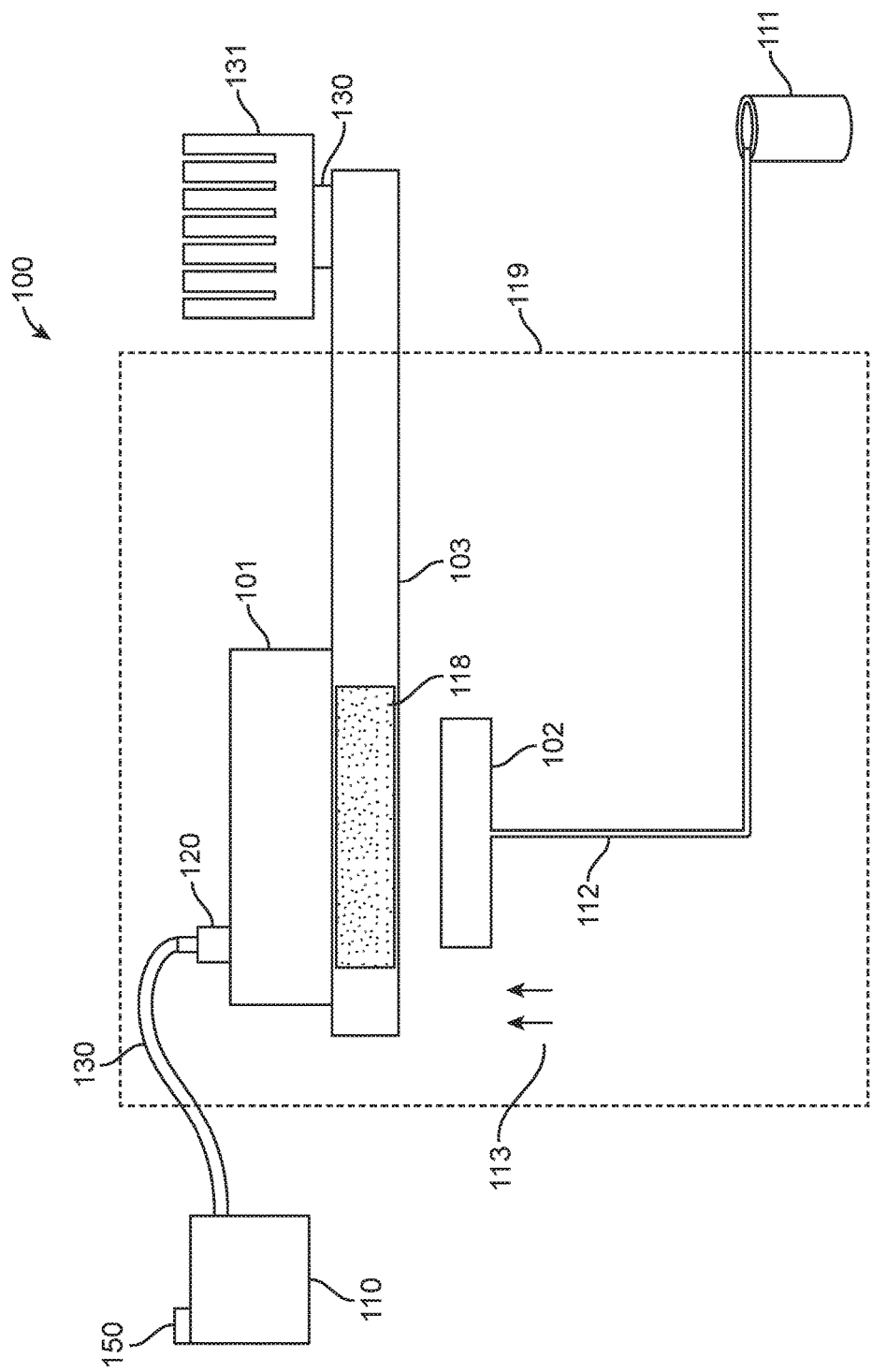
FIGS. 1A-1B show an exemplary embodiment of a sanitizer system.

FIG. 1A shows an exemplary embodiment of a sanitizer system 100. The sanitizer system comprises a cassette 101, a pressure control element 110, a heating element 102, and a cooling element 103. Cassette 101 may be removably disposed on the heating element or the cooling element of the sanitizer system. In FIG. 1A, cassette 101 is in surface contact with cooling element 103 and heating element 102 is in a lowered position relative to cooling element 103.

Figure 1B:
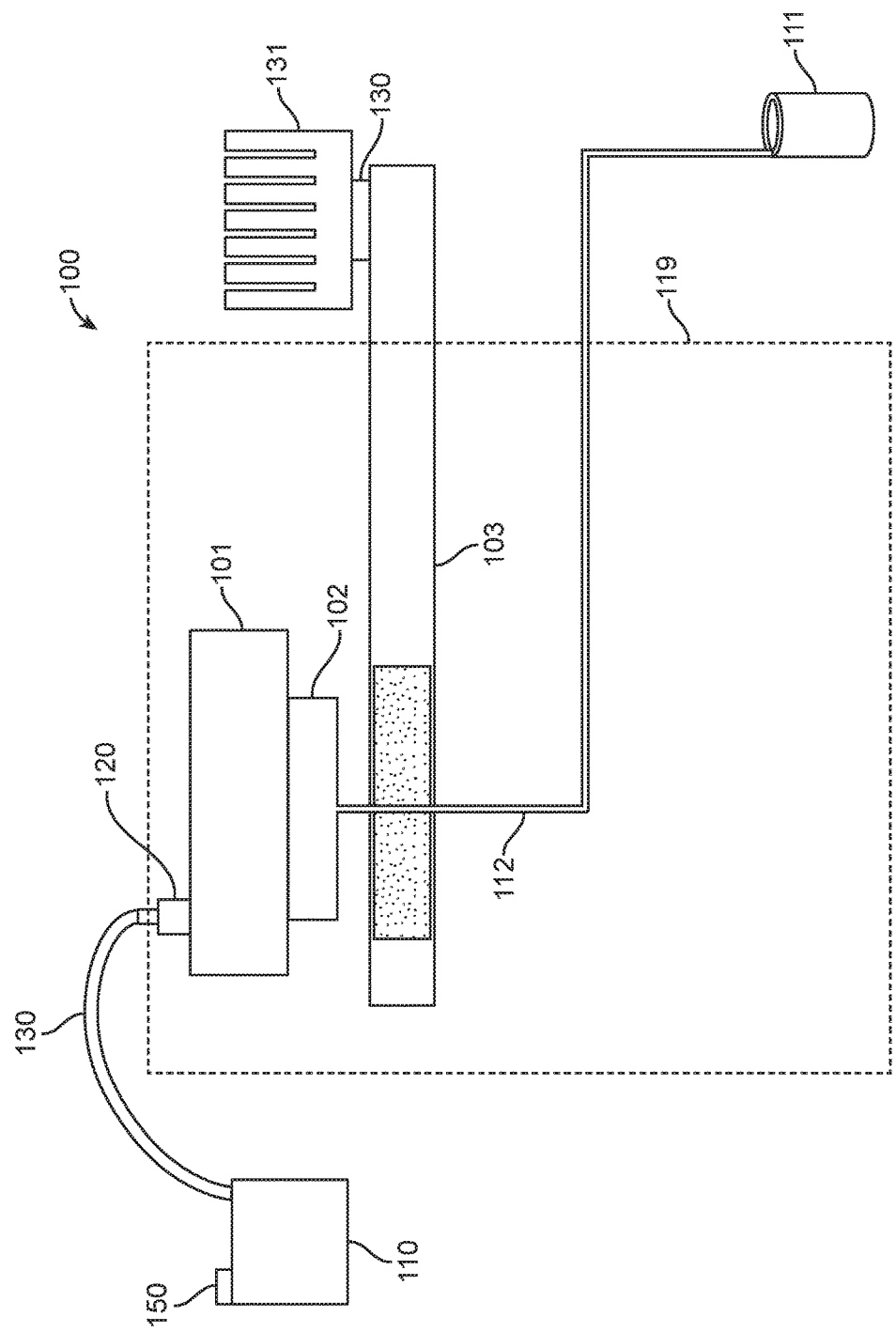

As shown in FIGS. 1A and 1B, the sanitizer system may further comprise an actuator element 111, wherein actuator element 111 is configured to move one of heating element 102 or cooling element 103 relative to the other of heating element 102 or cooling element 103 through for example a mechanical connection 112. In a preferable embodiment, the arrows 113 in FIG. 1A indicate the direction of movement of heating element 102 from an initial lowered position to a raised position relative to cooling element 103. Actuator element 111 may comprise, for example, a motor, cable/pulley, rack/pinion, hydraulic/pneumatic or any other device known in the art having the ability to move the heating or cooling element to a desired position.

Figure 1C:
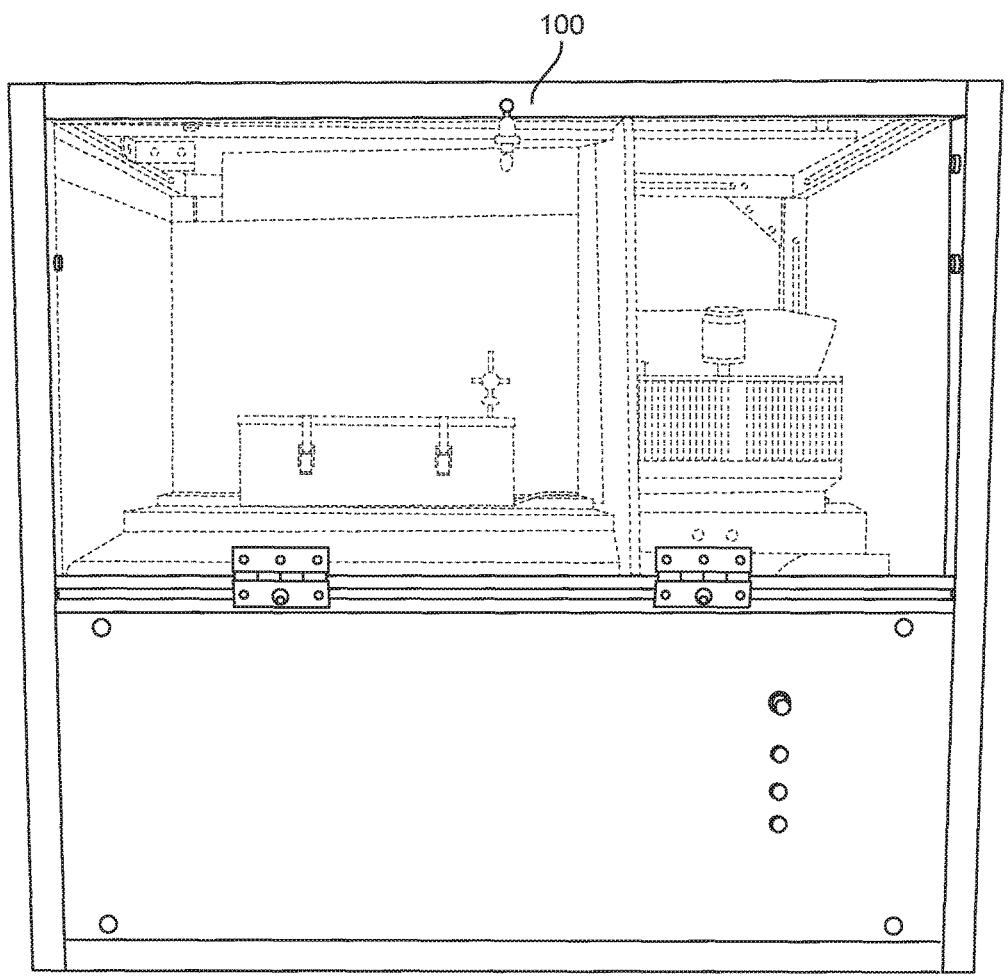
FIG. 1C shows a photograph of the exemplary embodiment of FIGS. 1A-1B.

FIG. 1B shows the exemplary embodiment of FIG. 1A wherein heating element 102 is in a raised position relative to cooling element 103 and cassette 101 is in surface contact with heating element 102. Note that, as depicted in FIGS. 1A and 1B, cassette 101 may only be in surface contact with one of the heating element 102 or cooling element 103 when it is in a raised or a lowered position with respect to the other of heating element 102 or cooling element 103. To facilitate this motion, one of the heating or cooling element may comprise an opening therein and the other of the heating or cooling element may be moved through the opening into a raised or lowered position relative to the heating or cooling element with the opening. FIG. 1C shows a photograph of the exemplary embodiment of a sanitizer system 100, as shown in FIGS. 1A-1B.

In an exemplary embodiment, the sanitizer system may use thermoelectric cooling that may actively cool a hot container or cassette thereby reducing the cool-to-cool total cycle time. The cooling element of the sanitizer system may comprise a cooling block 103, which may be comprised of any material with a high enough thermal conductivity for effective heat transfer. In a preferable embodiment, the cooling block may be comprised of brass. The cooling block 103 may be actively cooled via thermoelectric coolers 130, which in turn, may have their heat dissipated into heat sinks 131. The cooling block 103 may be one solid piece that extends through an opening into the enclosed environment 119.

The cooling element may be configured to be in surface contact with the cassette such that the cooling element reduces the temperature of the cassette. In addition, the cooling element may comprise a plurality of elongated cooling members separated by alternating gaps forming a cooling platform having a substantially planar cooling surface.

The pressure control element 110 may be configured to fluidly engage, through for example, pressure control engagement element 130 and valve 120, with cassette 101 in order to produce a pressure-controlled environment within an airtight chamber enclosed by the cassette. The pressure control element may comprise a vacuum or insertion element 110 configured to fluidly engage with cassette 101 and evacuate or insert fluid from the airtight chamber enclosed by the cassette to produce a vacuum or pressurized environment therein. The fluid may comprise a liquid or a gas, including but not limited to air, an inert gas, such as argon or neon, or a non-oxidizing gas, such as nitrogen. Vacuum or insertion element 110 may also comprise a valve (not shown) to control or monitor the chamber environment, wherein the valve is configured to provide an audible or visual indication that an airtight seal has been broken by actuating the valve from a closed position to an open position. Sanitizer system 100 may further comprise an indicator 150, such as, for example, a pressure gauge, having indicia that indicate a degree of vacuum or pressure established in the airtight chamber.

Figure 2A:
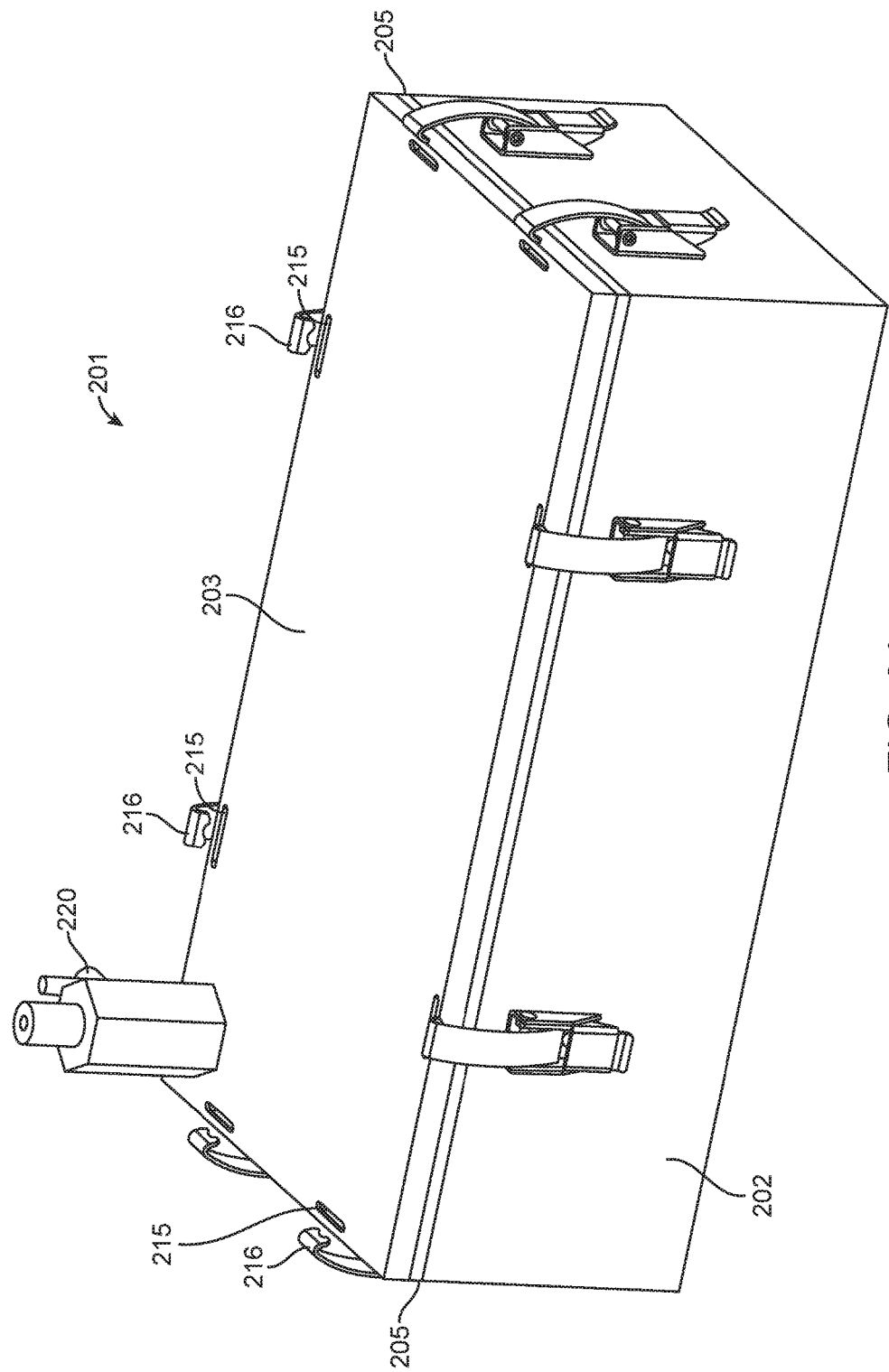
FIGS. 2A-2B show a perspective view of a cassette that may be used in an exemplary embodiment of a sanitizer system.
Figure 2B:
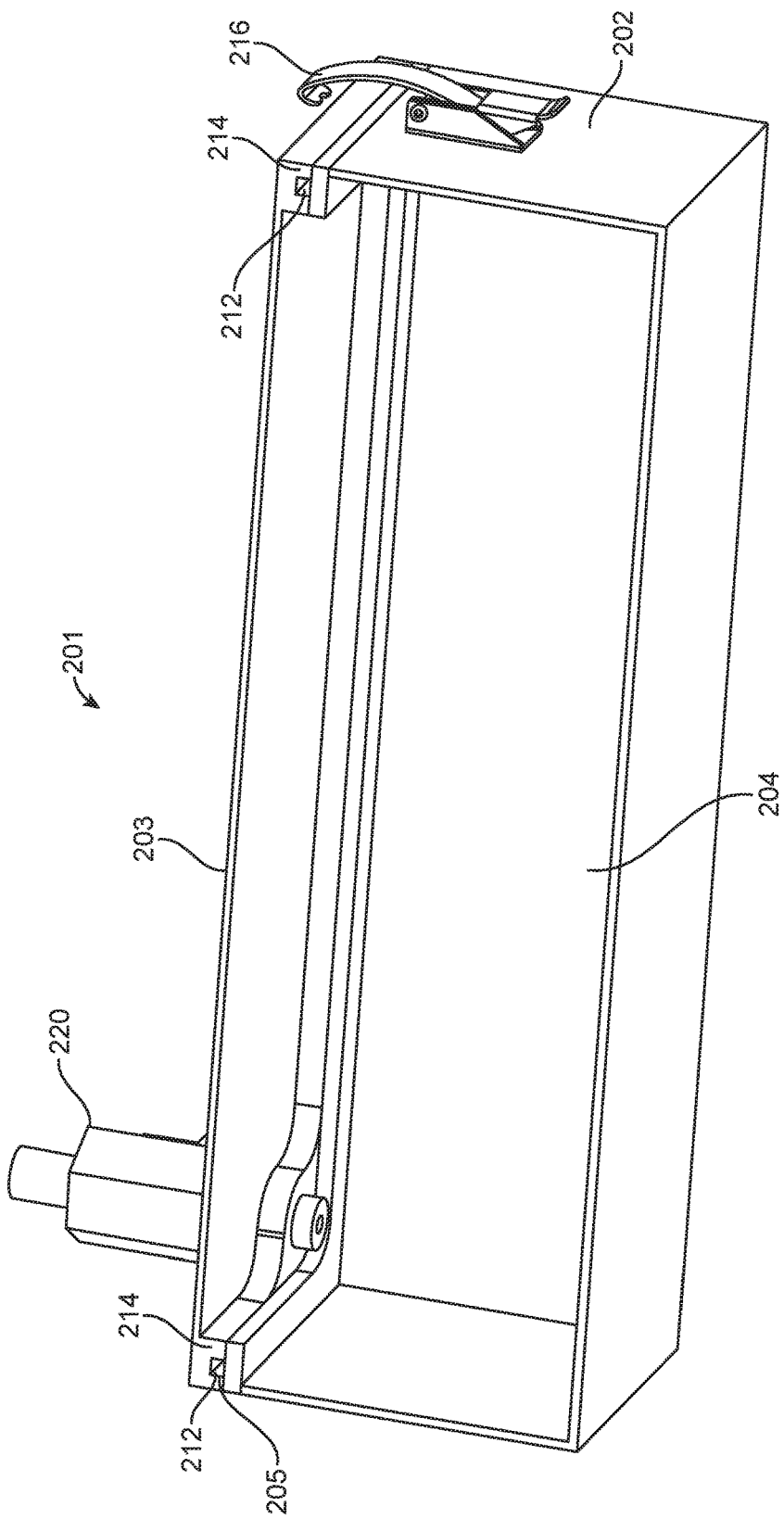

FIG. 2A shows a perspective view of a cassette 201 for use in an exemplary embodiment. Cassette 201 comprises a body 202 and a removable lid 203. FIG. 2B depicts a cross-sectional perspective view that shows the inside of the exemplary embodiment of FIG. 2A. In particular, as shown in FIG. 2B, cassette body 202 and removable lid 203 form an airtight chamber 204 when joined together, wherein the airtight chamber 204 is configured to contain an object or instrument for sanitization. Removable lid 203 may comprise a mating groove 212 configured to mate with a mating surface 214 on cassette body 202 to form an airtight seal 205. Mating groove 212 may be an O-ring groove containing an O-ring and mating surface 214 may be fabricated from stainless steel, which the O-ring seals against to form airtight seal 205. In addition, removable lid 203 may be held against cassette body 202 with cassette body engagement members 216, which may be attached to cassette body 202 and which are configured to engage with removable lid engagement members 215 in removable lid 203 (best seen in FIG. 2A). Cassette body engagement members 216 may be stainless steel toggle clamps that may be welded or otherwise attached to cassette body 202, which may also be fabricated from stainless steel, and cassette lid engagement members may be engagement grooves 215, wherein clamps 216 are configured to latch into engagement grooves 215. Notably, cassette body engagement members 216 and cassette lid engagement members 215 are not limited to clamps and grooves respectively. In particular, one of cassette body engagement member 216 or cassette lid engagement member 215 may comprise a protrusion or tab and the other of cassette body engagement member 216 or cassette lid engagement member 215 may comprise an opening, indentation, or recess configured to mate or join with the corresponding protrusion or tab.

FIGS. 3A and 3B show a top and cross-sectional side view respectively of a removable lid 303 for use in an exemplary embodiment. Removable lid 303 comprises a mating groove 312, which may be an O-ring groove and which may contain an O-ring (not shown). The lid 303 may easily be removed and replaced.

FIGS. 4A and 4B show a top and cross-sectional side view respectively of a cassette body 402 for use in an exemplary embodiment. Cassette body 402 comprises a mating surface 414 configured to mate with an O-ring in the O-ring groove, as depicted for example in FIGS. 3A and 3B, to form an airtight seal. Cassette body further comprises a valve 420 having the ability to be opened and closed. Cassette body 402 and mating surface 414 may both be fabricated using stainless steel. Valve 420 may also be stainless steel and may be welded to cassette body 402. Cassette body 402 may have no holes or perforations and may be one completely enclosed piece of stainless steel formed, for example, by folding and welding stainless steel sheet metal together in a desired geometry. Cassette body 402 may further comprise cassette engagement members 416, which may be stainless steel toggle clamps that may be welded to cassette body 402. Cassette body engagement members 416 are not limited to clamps but may also comprise protrusions or tabs, or alternatively, may comprise grooves, openings, indentations, or recesses configured to mate or join with a corresponding protrusion or a tab.

Figure 5:
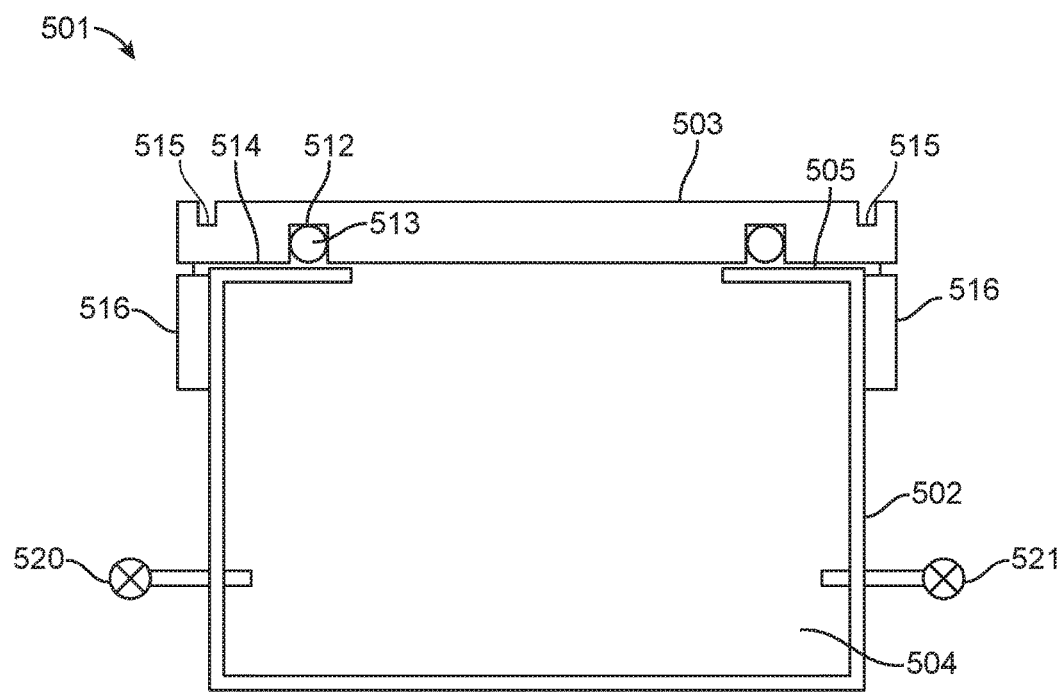
FIG. 5 shows a cross-sectional view of a cassette.

FIG. 5 shows a cross-sectional view of a cassette 501 comprising both a cassette body 502 and a removable lid 503 for use in an exemplary embodiment. Objects or instruments to be sanitized may be disposed in cassette 501. Cassette body 502 and removable lid 503 form an airtight chamber 504 when joined together, wherein the airtight chamber 504 is configured to contain an object or instrument for sanitization. Removable lid 503 may comprise a mating groove 512 configured to mate with a mating surface 514 on cassette body 502 to form an airtight seal 505. The mating groove may be an O-ring groove 512 containing an O-ring 513 and mating surface 514 may be fabricated from stainless steel, which O-ring 513 seals against to form airtight seal 505. In addition, removable lid 503 may be held against cassette body 502 with cassette body engagement members 516, which may be attached to cassette body 502 and which are configured to engage with removable lid engagement members 515. Cassette body engagement members may be stainless steel toggle clamps 516 that may be welded or otherwise attached to cassette body 502, which may also be fabricated from stainless steel, and removable lid engagement members may be engagement grooves 515, wherein clamps 516 are configured to latch into engagement grooves 515. Notably, cassette body engagement members 516 and cassette lid engagement members 515 are not limited to clamps and grooves respectively. In particular, one of cassette body engagement member 516 or cassette lid engagement member 515 may comprise a protrusion or tab and the other of cassette body engagement member 516 or cassette lid engagement member 515 may comprise an opening, indentation, or recess configured to mate or join with the corresponding protrusion or tab.

Valve 520 may be a ball valve that may be opened and connected to a pressure control element to create a vacuum or pressurized environment within the closed cassette shown in FIG. 5. Valve 520 may be closed while the chamber is under vacuum or under pressure, to create a chamber environment that is isolated from the ambient environment, essentially forming a mini vacuum or pressurized chamber that houses the objects or instruments. Cassette 501 may further comprise an alignment element on a top surface of the cassette (not shown) and a mating element on a bottom surface of the cassette (not shown) configured to align and mate with an adjacent cassette having an alignment element and a mating element. In particular, these alignment and mating elements would enable a cassette to be stacked on top of an adjacent cassette for storage or for other purposes where stacking cassettes would be advantageous or desirable.

The cassettes and their respective chambers may vary in shape, size, and material. A cassette may be made in any shape or geometry (e.g. cylindrical, spherical, box-shaped, or some other contoured or irregular shape having an internal volume) depending on the instruments and devices to be sanitized. A cassette may also be any size (e.g. large, medium, or small) suitable for containing the objects for sanitization or as required by the end user. For example, small cassettes may be used to hold one standard set or even one tool if desired and the cassettes may have locations where individual instruments may latch into or be secured onto the base of the cassette. Cassettes may also be large enough to house several commercially available containers. Additionally, a cassette may be made of any material suitable to be heated and cooled. For example, the removable lid and potentially even the sides of the cassette body may be constructed of a polymer or polymeric material, provided that the polymer can withstand higher temperatures as needed for sanitization, with only the base, which is in surface contact with the instruments, constructed of metal to allow heat to be conducted through the base to the instruments. The time required to cool the base of the cassette and instruments to a temperature appropriate for use of the instruments may be decreased if plastic or some other appropriate non-metallic material is used to construct portions of the cassette provided that there is less mass to cool as compared with a completely metallic cassette.

A preferable embodiment of a sanitizer system may further comprise a filter (not shown), which may sanitize the fluid within the airtight chamber 504. Cassette 501 may comprise both an input valve 520 and an output valve 521, wherein the input and the output valve may each have an open and a closed position, and wherein when both the input and the output valve are in the open position, filtered fluid may be configured to be delivered through the input valve filling the cassette with filtered fluid and forcing unfiltered fluid out of the output valve. The fluid may comprise a liquid or a gas, including but not limited to air, an inert gas, such as argon or neon, or a non-oxidizing gas, such as nitrogen.

The heating element for a sanitizer system may be in surface contact with the cassette and may also further comprise a plurality of elongated heating members separated by alternating gaps forming a heating platform having a substantially planar heating surface, wherein the heating platform conducts heat in a substantially even manner over a surface of the cassette. The heat provided by the heating element may raise the temperature within the airtight chamber of the sanitizer system to a temperature and for a period of time sufficient to sterilize the object for sanitization to a level suitable for dental use or surgical use.

Figure 6B:
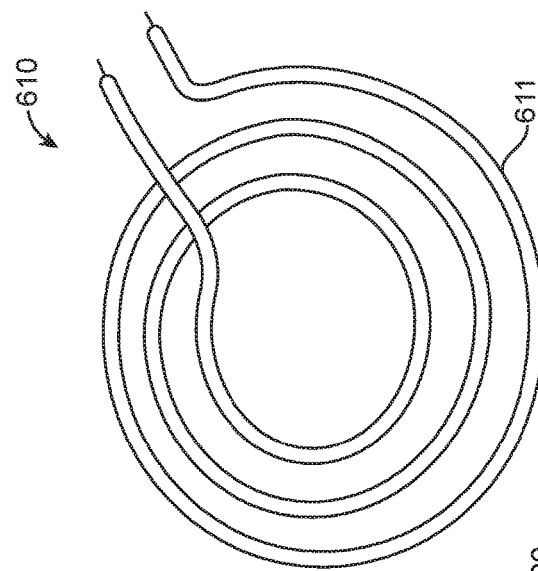
FIGS. 6A-6C show examples of heating element configurations.
Figure 6C:
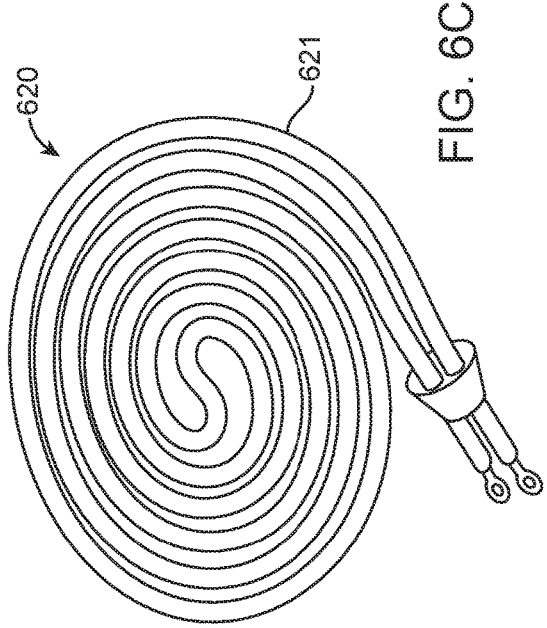
Figure 6A:
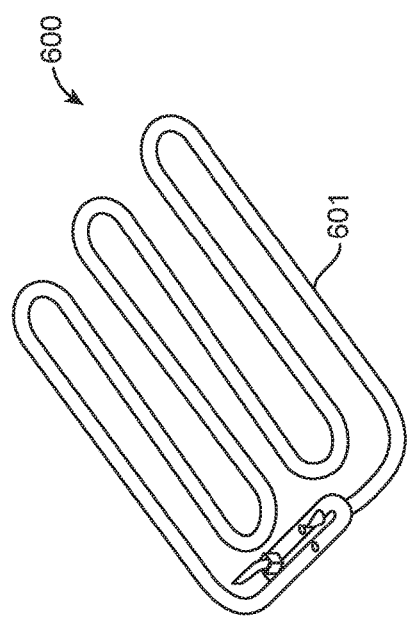

FIG. 6A shows an example of a configuration for a heating element 600 for a sanitizer system. The heating element may comprise an elongated member 601 in a serpentine or sinusoidal configuration as shown for example in FIG. 6A. Alternatively, elongated members 611 or 612 may be formed in a concentric circular or coiled configuration as shown for example in the heating elements 610 and 620 FIGS. 6B and 6C respectively. Note that, as described above, the cooling element may also comprise a plurality of elongated cooling members separated by alternating gaps forming a cooling platform having a substantially planar cooling surface. The elongated cooling members may further comprise an elongated member in a serpentine or sinusoidal configuration as shown for example in FIG. 6A, or in a concentric circular or coiled configuration as shown for example in FIGS. 6B-6C. Additionally, the elongated members of a heating element, formed for example by a serpentine or sinusoidal configuration as shown in FIG. 6A, may be configured to interdigitate with or be nested within the elongated members of an adjacent cooling element that may also be formed by a serpentine or sinusoidal configuration. This interdigitated or nested configuration may allow the elongated members of one of the heating element or the cooling element to pass between the elongated members of the other of the heating element or the cooling element when one of the heating element or the cooling element is raised or lowered with respect to the other of the heating element or the cooling element.

A heating element or cooling element in an embodiment of a sanitizer system as disclosed herein is not limited to the examples shown and may take various forms, shapes, configurations and sizes as known in the art.

FIGS. 7A and 7B show a top and cross-sectional front view respectively of a removable lid 703 for use in an exemplary embodiment, wherein a heating element 702 is disposed inside the cassette to heat the airtight chamber from within. Removable lid 703 may further comprise electrical contacts 725 exiting the lid 703 of the cassette through sealed openings 735. Removable lid 703 may comprise a mating groove 712, which may be an O-ring groove and which may contain an O-ring (not shown) configured to mate with a mating surface of the cassette body.

One of ordinary skill in the art will appreciate that embodiments of the present disclosure may be constructed of materials known to provide, or predictably manufactured to provide, the various aspects of the present disclosure. For example, an embodiment of a sanitizer system may be manufactured using methods and techniques comprising injection molding, computer-numeric control (CNC) machining, and 3-D printing.

Figure 8:
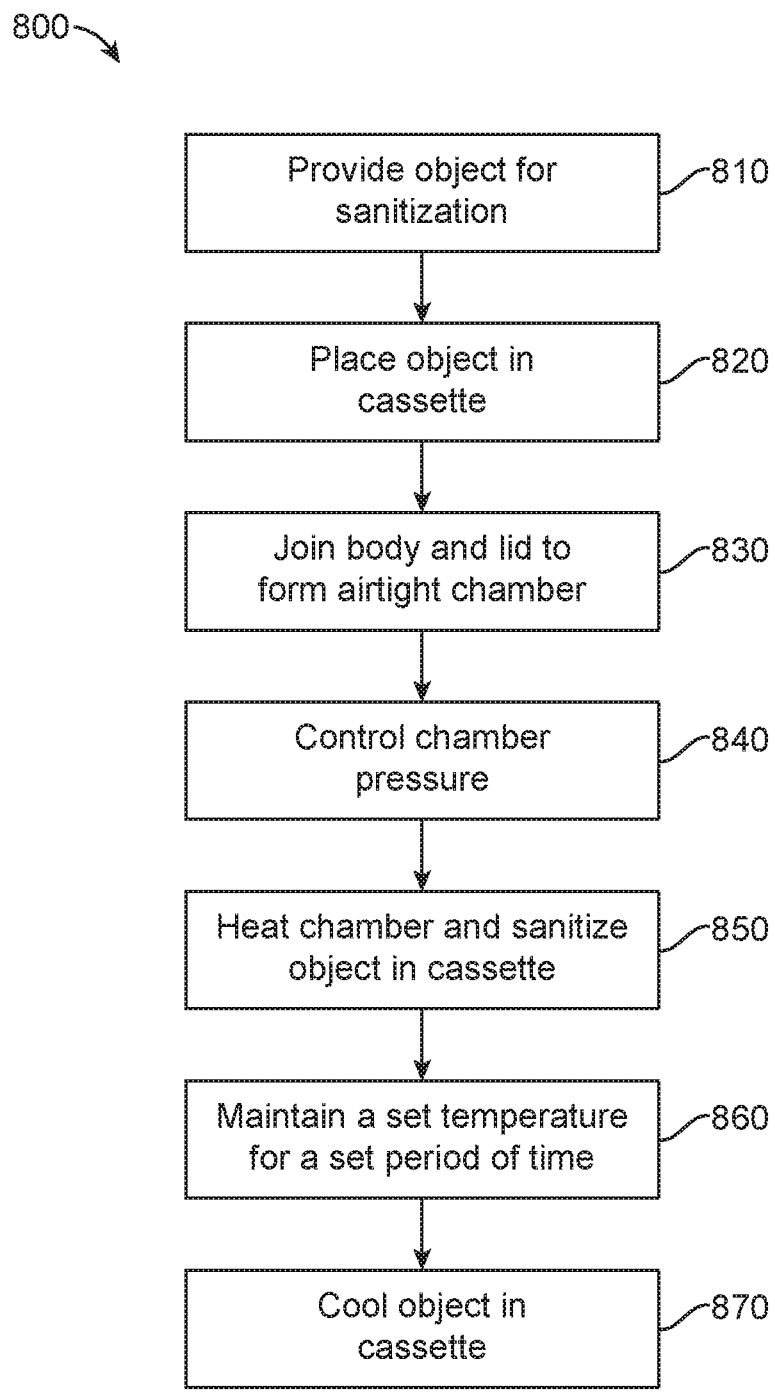
FIG. 8 shows a flow chart for an exemplary embodiment of a method of sterilization or sanitization.

FIG. 8 shows an embodiment of a method of sanitizing an object. The method 800 comprises: providing an object for sanitization 810; placing the object for sanitization within a cassette comprising a body and a removable lid at 820; joining the body and removable lid of the cassette to form an airtight chamber containing the object for sanitization at 830; controlling a pressure in the airtight chamber at 840; heating the airtight chamber using a heating element to raise the temperature within the airtight chamber and thereby sanitizing the object for sanitization contained within the airtight chamber at 850; maintaining the temperature for a designated period of time sufficient to sanitize the object for sanitization at 860; and cooling the object for sanitization at 870.

In a preferable embodiment of a method of sanitizing an object, providing an object for sanitization at 810 may comprising taking instruments that have been scrubbed, washed, and chemically treated in accordance with any requirements, laws, and regulations applicable to the respective standard for sanitization employed in the industry and placing them in a cassette (as shown for example in FIG. 2A and FIG. 5).

Joining the body and removable lid of the cassette to form an airtight chamber may comprise placing the lid (as shown for example in FIGS. 3A-3B) on the cassette body (as shown for example in FIGS. 4A-4B) so that an O-ring on the lid forms an airtight seal with a mating surface on the cassette body, enclosing the instruments in an airtight chamber as shown in FIG. 5. As depicted and described above in FIGS. 2A-2B and FIG. 5, cassette body engagement members 216 and 516 may be toggle clamps that may comprise rings that can be looped over removable lid engagement members 215 and 516, which may be engagement grooves 515 in the removable lid. The toggle clamps may then be locked down to form an airtight seal between the O-ring groove 512 of removable lid 512 and the mating surface 514 of the cassette body, as shown in FIG. 5. Notably, the method is not limited to the clamps and grooves as described above, but any method to form and maintain an airtight seal between the removable lid and the cassette body as known in the art may be employed, including for example, using the internal vacuum generated in the chamber or the weight of the lid. The O-ring or other sealing material used to form an airtight seal between the removable lid and the cassette body need only satisfy any requirements, laws, and regulations applicable to the respective standard for sanitization employed in the industry.

Controlling a pressure in the airtight chamber at 840 may comprise evacuating fluid from or disposing fluid into the airtight chamber to either decrease or increase the pressure in order to produce a vacuum or pressurized environment within the airtight chamber. In a preferable embodiment, controlling the pressure may comprise turning a valve 120 as shown in FIGS. 1A-1B into an open position to allow air to flow in and out of the chamber through the valve. At this point, air will only be able to flow in and out of the cassette through the valve because the O-ring has formed an airtight seal between the removable lid and the cassette body. Controlling the pressure may further comprise connecting a nipple of valve 120, with the valve still in an open position, to an insertion element 110, which may be a vacuum pump, so as to evacuate air from the chamber. After the cassette has been evacuated as much as possible and with the vacuum pump 110 still on and connected to the nipple of valve 120, the valve may be turned to a closed position. The vacuum pump may be turned off and disconnected from the nipple of the valve leaving the instruments resting at the bottom of an evacuated cassette chamber with a pressure different from atmosphere.

The method may further comprise controlling or monitoring the vacuum or pressurized environment within the airtight chamber after the object for sanitization has been sanitized by using an audible or visual indicator that the cassette is still under vacuum or is still pressurized. Additionally, as shown in FIG. 5, the cassette may comprise an input valve 520 and an output valve 521, and method may further comprise: opening the input valve, opening the output valve, passing a filtered fluid through the input valve into the chamber, forcing unfiltered fluid from the chamber through the output valve, pressurizing the chamber, and closing both valves. The fluid may comprise a liquid or a gas, including but not limited to air, an inert gas, such as argon or neon, or a non-oxidizing gas, such as nitrogen.

Heating the airtight chamber at 850 may comprise heating the airtight chamber through thermal conduction, through thermal convection, by contacting a surface of the cassette with the heating element, or by heating with the heater element disposed inside the cassette. In a preferable embodiment, the cassette may first be placed on the cooling element 103 of the sanitizer system 100 shown in FIG. 1A. At this time, cooling element 103 is at room temperature because the system has not been turned on. The sanitizer system 100 may be turned on in order to activate the actuator 111 to raise the heating element 102 up through an opening in the cooling element 103 where cassette 101 was initially placed. Heating element 102 makes surface contact with and supports cassette 101, raising the cassette above cooling element 103 so that the cassette is now only resting on heating element 102, as shown in FIG. 1B. At this point, only heating element 102 is in surface contact with cassette 101.

Heating element 102 may be turned on and set to a designated or desired temperature for an appropriate time to sanitize or sterilize the instruments disposed in cassette 101 to a level suitable for dental use or surgical use. Heating may be accomplished in any fashion as long as it is compliant with the allotted amount of time at the appropriate temperature to ensure sanitization or sterilization. Temperature ranges appropriate for sanitizing instruments include 340° F. for a minimum of 60 minutes, preferably 360° F. for a minimum of 30 minutes, and more preferably 375° F. for a minimum of 6 minutes to ensure that the instruments are sterilized. Commercially available indicators may be used to ensure that the temperature of the cassette chamber has reached an appropriate sanitization or sterilization temperature for a sufficient time to sanitize or sterilize the instruments for surgical, dental, or any other desired use. These indicators may be placed on the bottom of the cassette with the instruments. If there is concern about the entire chamber environment being heated, an indicator could be placed on top of a material with a low thermal conductivity that can withstand the higher temperature such as a plastic. The indicator will therefore not be heated via conduction through the base of the cassette but through both convection and radiation within the box ensuring that the entire environment within the cassette has reached a particular temperature indicative of being sanitized or sterilized. The method may also use a controller or any means known to those skilled in the art to monitor and/or control the sanitization process or elements (e.g. the heating element or the cooling element) such as by use of programmable logic controllers.

Figure 9:
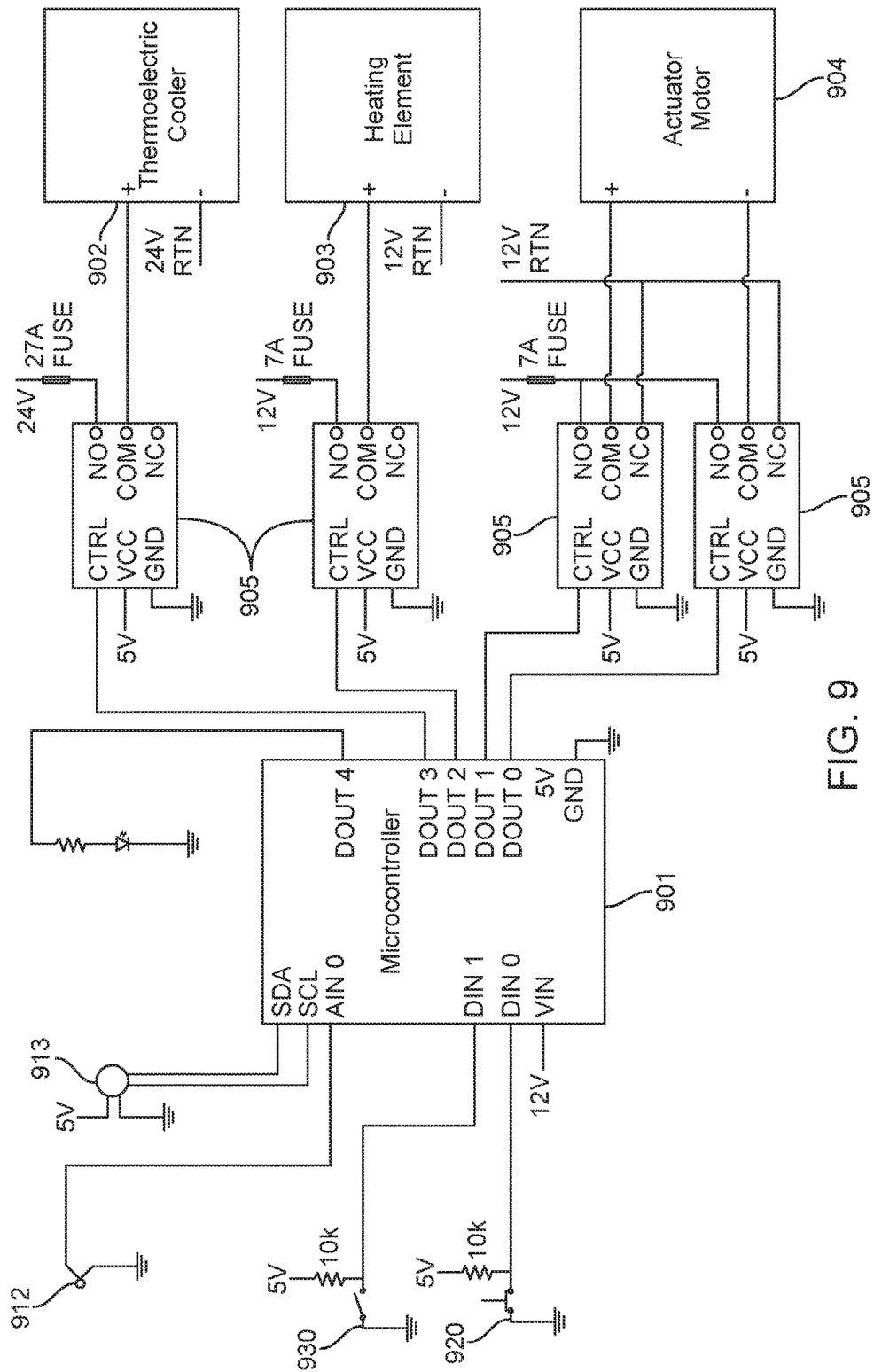
FIG. 9 shows a block diagram of components for monitoring and controlling a sanitizer/sterilizer system.

FIG. 9 shows an embodiment of a sanitizer system that uses a controller to monitor and/or control the sanitization process and elements thereof Microcontroller 901 may be connected to and may be used to control thermoelectric cooler 902, heating element 903, and actuator motor 904 through relay boards 905. In addition, microcontroller 901 may receive inputs from: start/stop push button 920, which may be used to activate the sanitizer system; contact switch 930, which may be used to indicate a safety interlock on the actuator in lifting the cassette to the heating element; and thermocouple/temperature sensor 912 and infrared contactless temperature sensor 913, which may be used to monitor the temperature of the cassette chamber.

In a preferable embodiment, cassette 101 may be heated through conduction by surface contact with heating element 102. The required temperature may be maintained for a designated period of time sufficient to sanitize or sterilize the instruments at 860, after which heating element 102 may be turned off and the actuator 111 may be activated to lower cassette 101 down to rest back in its original position on cooling element 103 as shown in FIG. 1A.

The instruments for sanitization may be disposed inside the cassette 101, and in particular, may rest on the bottom of cassette 101 and may be heated through conduction via contact with the bottom of cassette 101. Additionally, the cassette may comprise support elements (not shown), including for example, holders or racks for supporting or holding the instruments. The support elements may be used for example to prevent unwanted movement of the instruments, to isolate the instruments from touching one another, or to keep the instruments in a desired order or configuration during the sanitization process or during storage.

Alternatively, the cassette may be heated in a conventional dry heat convection oven, wherein the cassette is heated by convection and the targeted objects for sanitization (e.g. medical instruments) contained within the cassette are heated by conduction.

It is also worth noting that cooling the object for sanitization at 870 may be accomplished in a multitude of fashions and need not be separate from the heating element. For example, a cooling jacket may be provided that rests on or is otherwise in communication with the heating element such that when the heating element is turned off, a pneumatic valve opens, allowing coolant fluid to flow into the cooling jacket to cool the cooling element and the cassette. Alternatively, an office water supply, a closed loop water circulation system connected to a refrigerator, or some other coolant fluid source as known in the art may be used to flow coolant fluid through the cooling jacket.

In a preferable embodiment, the cassette may be metallic and thus, along with being heated via conduction, it may also be actively cooled through conduction reducing the overall cool-to-cool total cycle time. In this case, cooling the object for sanitization at 870 may comprise activating thermoelectric coolers 130 to actively cool the cooling element 103 which is now in surface contact with cassette 101 as shown in FIG. 1A. Heat is removed from the instruments and cassette 101 through conduction via cooling element 103, which is in turn cooled by thermoelectric coolers 130.

The thermoelectric coolers 130 may remain on for a time sufficient to allow enough heat to be removed from the cassette as well as the instruments the cassette is housing so that they are at room temperature. Radiative heat sinks 131 may be used to dissipate heat from thermoelectric coolers 130. Both the thermoelectric coolers and heat sinks may be located outside the enclosed environment 119 where the cassette is being heated to ensure that the thermoelectric coolers do not exceed their maximum operation temperature. The heating element, which is mechanically connected to an actuator, remains off at this stage and is disposed below the cooling element.

Additionally, programmable logic may be used to simplify the end user's experience for the heating and cooling of the cassette chamber in the sanitizer system. For example, the logic may provide error codes in the case of failure to simplify trouble shooting.

Once cassette 101 and the instruments disposed therein return to room temperature, the cassette may be removed from the sanitizer system. The instruments disposed in the cassette have thus been sanitized and returned to room temperature while still under vacuum or pressure, and are ready for use or storage. The cassette may be stored on top of an adjacent cassette.

The system may utilize any means known to those skilled in the art to handle the loading and/or unloading of the cassette from or onto the heating element or the cooling element. The sanitizer system may also be used to cool more than one cassette at a time and may be enlarged to sanitize several cassettes.

The temperature of the cassette may be monitored at all times for safety to ensure that no one picks up a hot cassette. Temperature may be monitored via thermocouples, infrared lasers, color changing indicators which are blue when cold and red when hot, or any other temperature sensing indicator known in the art or commercially available.

When ready to remove the instruments from the cassette for use, valve 120 may be turned to an open position. Air from the ambient environment will rush into cassette 101 through the nipple of valve 120 until the pressure within the chamber of cassette 101 and the pressure external to cassette 101 are substantially the same, so as to reach equilibrium. A rush of the air into cassette 101 through valve 120 may provide an audible signal that the instruments inside cassette 101 have not been contaminated by the ambient environment. In a preferable embodiment, along with the audible signal, a visual gauge (digital or analog), or tactile signal (i.e. discernable to the touch) may also be provided to indicate that the seal has held and the airtight chamber has not been compromised or otherwise contaminated by the ambient environment. The audible sound may also be enhanced by manipulating the nipple of the valve to make a whistle noise or other audible sound.

Once valve 120 is open and the chamber of cassette 101 has reached equilibrium by equalizing the pressure in the chamber with the ambient environment, the clamps or other cassette engagement members may be loosened from the removable lid and the lid may be detached from the cassette body. Once the lid has been detached and removed from the cassette body the instruments may be removed from the cassette 101 and are ready for use.

The sanitizer system may be used to sterilize and/or store dental and/or orthodontic instruments. The sanitizer system may also be configured to comply with or satisfy US government regulatory requirements and/or standards including: ANSI/AAMI/ISO 20857: 2010 (sterilization of health care products—dry heat: requirements for the development, validation and routine control of an industrial sterilization process for medical devices); and ANSI/AAMI ST40:2004/(R) 2010 (Table-top dry heat (heated air) sterilization and sterility assurance in health care facilities, $2^{nd}$ ed).

The cassette used in the sanitizer system isolates the instruments from the ambient environment before, during, and after sanitation. Because the cassette may also be used as a storage unit, there is no need to transfer the sanitized instruments to plastic bags or to any other sterile container known in the art. In addition, the sanitizer system reduces the cool-to-cool total cycle time resulting in faster sanitization turnaround times and a reduction in the number of instruments needed by an office to maintain a desired patient flow.

One of ordinary skill in the art will appreciate that embodiments of the present disclosure as provided in FIGS. 1-9 are not limited for use in dental and/or orthodontic applications, but may be applied for other purposes and to many other industries. For example, the sanitizer system may be used in hospital settings, surgical settings, veterinary applications, food preparation, electronics, pharmaceutical, aerospace and any application requiring the sanitization or sterilization and/or storage of sanitized or sterilized instruments, components, or systems.

As will be appreciated, any feature may be used alone or in combination with another feature disclosed herein.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

While preferred embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of sanitizing an object comprising:
providing an object for sanitization;
placing the object for sanitization within a cassette comprising a body and a removable lid such that the object for sanitization is in surface contact with the cassette;
joining the body and removable lid of the cassette to form an airtight chamber containing the object for sanitization;
controlling a pressure in the airtight chamber;
heating the airtight chamber using a heating element to raise the temperature within the airtight chamber and thereby sanitizing the object for sanitization contained within the airtight chamber;
maintaining the temperature for a designated period of time sufficient to sanitize the object for sanitization; and
cooling the object for sanitization, wherein cooling the object for sanitization further comprises contacting a surface of the cassette with a cooling element; and
further comprising moving one of the heating element or the cooling element relative to the other of the heating element or cooling element such that the cassette is only in surface contact with either the heating element or the cooling element.

2. The method of claim 1, wherein said heating the airtight chamber comprises heating the airtight chamber through thermal conduction.

3. The method of claim 1, wherein said heating the airtight chamber comprises heating the airtight chamber through thermal convection.

4. The method of claim 1, wherein said heating the airtight chamber comprises heating with the heating element disposed inside the cassette.

5. The method of claim 1, wherein said controlling the pressure in the airtight chamber comprises evacuating fluid from the airtight chamber to decrease the pressure and to produce a vacuum environment therein.

6. The method of claim 5, further comprising controlling or monitoring the vacuum environment within the airtight chamber after the object for sanitization has been sanitized by using an audible or visual indicator that the cassette is still under vacuum.

7. A method of sanitizing an object comprising:
providing an object for sanitization;
placing the object for sanitization within a cassette comprising a body and a removable lid;
joining the body and removable lid of the cassette to form an airtight chamber containing the object for sanitization;
controlling a pressure in the airtight chamber;
heating the airtight chamber using a heating element to raise the temperature within the airtight chamber and thereby sanitizing the object for sanitization contained within the airtight chamber;
maintaining the temperature for a designated period of time sufficient to sanitize the object for sanitization;
cooling the object for sanitization, wherein cooling the object for sanitization further comprises contacting a surface of the cassette with a cooling element;
wherein the cassette comprises an input valve and an output valve, and wherein the method further comprises: opening the input valve, opening the output valve, passing sanitized fluid through the input valve into the airtight chamber, forcing fluid from the airtight chamber through the output valve, pressurizing the airtight chamber, and closing both valves; and
moving one of the heating element or the cooling element relative to the other of the heating element or cooling element such that the cassette is only in surface contact with either the heating element or the cooling element.

8. The method of claim 7, wherein said heating the airtight chamber comprises heating the airtight chamber through thermal conduction.

9. The method of claim 7, wherein said heating the airtight chamber comprises heating the airtight chamber through thermal convection.

10. The method of claim 7, wherein said heating the airtight chamber comprises heating with the heating element disposed inside the cassette.

11. The method of claim 7, further comprising stacking the cassette on top of an adjacent cassette.

12. The method of claim 7, further comprising sterilizing the object for sanitization to a level suitable for dental use or surgical use.

13. The method of claim 7, wherein said cooling the object for sanitization comprises actively cooling the object for sanitization.

* * * * *